United States Patent [19]

Larsen

[11] Patent Number: 5,002,887
[45] Date of Patent: Mar. 26, 1991

[54] TRUNCATED THROMBOLYTIC PROTEINS

[75] Inventor: Glenn R. Larsen, Sudbury, Mass.

[73] Assignee: Genetics Institute, Inc., Cambridge, Mass.

[21] Appl. No.: 882,051

[22] Filed: Jul. 3, 1986

Related U.S. Application Data

[63] Continuation-in-part of Ser. No. 825,104, Jan. 31, 1986, abandoned, which is a continuation-in-part of Ser. No. 853,781, Apr. 18, 1986, abandoned, which is a continuation-in-part of Ser. No. 861,699, May 9, 1986, abandoned.

[51] Int. Cl.$^5$ .............................................. C12N 9/48
[52] U.S. Cl. .................................... 435/212; 435/215; 435/217; 435/226; 435/172.3; 424/94.64; 424/94.63; 536/27; 935/10; 935/14
[58] Field of Search ............... 435/212, 215, 217, 226, 435/172.3; 935/10, 14, 70; 424/94.64, 94.63; 536/27

[56] References Cited

FOREIGN PATENT DOCUMENTS

| | | |
|---|---|---|
| 0225286 | of 0000 | European Pat. Off. |
| 0227462 | of 0000 | European Pat. Off. |
| 0041766 | 12/1981 | European Pat. Off. ............. 435/212 |
| 0093619 | 11/1983 | European Pat. Off. ............. 435/212 |
| 0207589 | 1/1987 | European Pat. Off. ......... 435/172.3 |
| 8401786 | 5/1984 | World Int. Prop. O. ......... 435/212 |

OTHER PUBLICATIONS

Pennica, D. et al., *Nature*, vol. 301, pp. 214–221, 1983.
Zoller, M. et al., *Nuc. Acid Res.*, vol. 10, pp. 6487–6500, 1982.
Pohl, G. et al., *Biochemistry*, vol. 23, pp. 3701–3707, 1984.
Kagitani et al., *Febs Letter*, vol. 189, pp. 145–149, Sept. 1985.
Ny, J. et al., *Proc. Natl. Acad. Sci.*, vol. 81, pp. 5355–5359, 1984.
Smith, G. et al., *Molec. & Cell Biol.*, vol. 3, pp. 2156–2165, 1983.
van Zonneveld et al., *J. Cell. Biochemistry*, vol. 32, pp. 169–178, 1986.
Klausner, A., *Biotechnology*, vol. 4, pp. 706–711, Aug. 1986.
Berman, P. et al., *Trends in Biotechnology*, vol. 3, pp. 51–53, Feb. 1985.

(List continued on next page.)

*Primary Examiner*—Richard A. Schwartz
*Assistant Examiner*—Nancy Treptow
*Attorney, Agent, or Firm*—Bruce M. Eisen; Luann Cserr

[57] ABSTRACT

Thrombolytic proteins are disclosed which have tissue plasminogen-type activity. The proteins are characterized by the presence of 0, 1, 2 or 3 N-linked polysaccharide substituents covalently bonded thereto and by a polypeptide sequence of the formula (a)A-R$^1$-B-R$^2$-C-R$^3$D wherein A, B, C, and D are the following polypeptide sequences substantially as shown in FIG. 1:
  A is Gly$_{-3}$ or Ser$_1$ through Trp$_{116}$, encompassing domain a;
  B is Ala$_{120}$ through Gly$_{183}$;
  C is Ala$_{187}$ through Leu$_{447}$;
  D is Val$_{451}$ through Pro$_{527}$; and
a is a peptide domain comprising a sequence of 0–93 amino acids selected from the sequence Gly$_{-3}$ or Ser$_1$ through Thr$_{91}$; R$^1$, R$^2$ and R$^3$ are each a tripeptide sequence linking said A, B, C and D by peptide bonds, up to three of R$^1$, R$^2$ and R$^3$ being a tripeptide sequence other than Asn-X-Thr or Asn-X-Ser, wherein X is any amino acid. Methods for making these proteins are disclosed as are therapeutic compositions containing same.

34 Claims, 4 Drawing Sheet

OTHER PUBLICATIONS

Opdenakker et al., *EMBO Workshop on Blasminogen Activators*, Amalfi, Italy, Oct., 1985, "The Carbohydrate Side Chains of TPA Influence at Activity".

van Zonneveld et al., *International Congress for the Society on Thrombosis and Hameostasis*, Abstract 022 as evident of presentation, Jul. 15, 1985.

van Zonneveld et al., *Proc. Natl. Acad. Sci* (PNAS), vol. 83, pp. 4670–4674, Jul. 1986.

Vehar et al, Cold Spring Harbor Symp. Quant Biol, vol. LI: 551–62.

Verheijen et al, 1986, EMBO J 5:3525–3530.

Rijken et al, 1986 Biochem J 238:643–646.

Little et al., 1984, Biochem 23: 6191–6195.

Harris et al, 1986, Mol Biol Med 3:279–292.

WO 86/01538 (Rosa et al/Biogen).

Tate et al, 1987, Biochem 26: 338–343.

Kaufman et al, 1985, Mol Cell Biol 5(7):1750–1759.

Banyai et al, 1983, FEBS 163: 37–41.

EP 0 042 246 (Guarente et al).

EP 0 178 105 (Wei et al/Integrated Genetics).

EP 0 174 835 (Gill et al, Upjohn).

FIGURE 1A

GTCGACCGGC AGGGGTGTGG GGAGCTCAGA GCTGAGATCC TACAGGAGTC

CAGGGCTGGA GAGAAAACCT CTGCGAGGAA AGGGAAGGAG CAAGCCGTGA

```
                                        MET Asp Ala MET Lys Arg
ATTTAAGGGA CGCTGTGAAG CAATC ATG GAT GCA ATG AAG AGA

Gly Leu Cys Cys Val Leu Leu Leu Cys Gly Ala Val Phe Val
GGG CTC TGC TGT GTG CTG CTG CTG TGT GGA GCA GTC TTC GTT

Ser Pro Ser Gln Glu Ile His Ala Arg Phe Arg Arg Gly Ala
TCG CCC AGC CAG GAA ATC CAT GCC CGA TTC AGA AGA GGA GCC

Arg Ser Tyr Gln Val Ile Cys Arg Asp Glu Lys Thr Gln MET
AGA TCT TAC CAA GTG ATC TGC AGA GAT GAA AAA ACG CAG ATG

Ile Tyr Gln Gln His Gln Ser Trp Leu Arg Pro Val Leu Arg
ATA TAC CAG CAA CAT CAG TCA TGG CTG CGC CCT GTG CTC AGA

Ser Asn Arg Val Glu Tyr Cys Trp Cys Asn Ser Gly Arg Ala
AGC AAC CGG GTG GAA TAT TGC TGG TGC AAC AGT GGC AGG GCA

Gln Cys His Ser Val Pro Val Lys Ser Cys Ser Glu Pro Arg
CAG TGC CAC TCA GTG CCT GTC AAA AGT TGC AGC GAG CCA AGG

Cys Phe Asn Gly Gly Thr Cys Gln Gln Ala Leu Tyr Phe Ser
TGT TTC ACC GGG GGC ACC TGC CAG CAG GCC CTG TAC TTC TCA

Asp Phe Val Cys Gln Cys Pro Glu Gly Phe Ala Gly Lys Cys
GAT TTC GTG TGC CAG TGC CCC GAA GGA TTT GCT GGG AAG TGC

Cys Glu Ile Asp Thr Arg Ala Thr Cys Tyr Glu Asp Gln Gly
TGT GAA ATA GAT ACC AGG GCC ACG TGC TAC GAG GAC CAG GGC

Ile Ser Tyr Arg Gly Thr Trp Ser Thr Ala Glu Ser Gly Ala
ATC AGC TAC AGG GGC ACG TGG AGC ACA GCG GAG AGT GGC GCC

Glu Cys Thr Asn Trp Asn Ser Ser Ala Leu Ala Gln Lys Pro
GAG TGC ACC AAC TGG AAC AGC AGC GCG TTG GCC CAG AAG CCC
```

FIGURE 1B

```
Tyr Ser Gly Arg Arg Pro Asp Ala Ile Arg Leu Gly Leu Gly
TAC AGC GGG CGG AGG CCA GAT GCC ATC AGG CTG GGC CTG GGG

Asn His Asn Tyr Cys Arg Asn Pro Asp Arg Asp Ser Lys Pro
AAC CAC AAC TAC TGC AGA AAC CCA GAT CGA GAC TCA AAG CCC

Trp Cys Tyr Val Phe Lys Ala Gly Lys Tyr Ser Ser Glu Phe
TGG TGC TAC GTC TTT AAG GCG GGG AAG TAC AGC TCA GAG TTC

Cys Ser Thr Pro Ala Cys Ser Glu Gly Asn Ser Asp Cys Tyr
TGC AGC ACC CCT GCC TGC TCT GAG GGA AAC AGT GAC TGC TAC

Phe Gly Asn Gly Ser Ala Tyr Arg Gly Thr His Ser Leu Thr
TTT GGG AAT GGG TCA GCC TAC CGT GGC ACG CAC AGC CTC ACC

Glu Ser Gly Ala Ser Cys Leu Pro Trp Asn Ser MET Ile Leu
GAG TCG GGT GCC TCC TGC CTC CCG TGG AAT TCC ATG ATC CTG

Ile Gly Lys Val Tyr Thr Ala Gln Asn Pro Ser Ala Gln Ala
ATA GGC AAG GTT TAC ACA GCA CAG AAC CCC AGT GCC CAG GCA

Leu Gly Leu Gly Lys His Asn Tyr Cys Arg Asn Pro Asp Gly
CTG GGC CTG GGC AAA CAT AAT TAC TGC CGG AAT CCT GAT GGG

Asp Ala Lys Pro Trp Cys His MET Leu Lys Asn Arg Arg Leu
GAT GCC AAG CCC TGG TGC CAC ATG CTG AAG AAC CGC AGG CTG

Thr Trp Glu Tyr Cys Asp Val Pro Ser Cys Ser Thr Cys Gly
ACG TGG GAG TAC TGT GAT GTG CCC TCC TGC TCC ACC TGC GGC

Leu Arg Gln Tyr Ser Gln Pro Gln Phe Arg Ile Lys Gly Gly
CTG AGA CAG TAC AGC CAG CCT CAG TTT CGC ATC AAA GGA GGG

Leu Phe Ala Asp Ile Ala Ser His Pro Trp Gln Ala Ala Ile
CTC TTC GCC GAC ATC GCC TCC CAC CCC TGG CAG GCT GCC ATC

Phe Ala Lys His Arg Arg Ser Pro Gly Glu Arg Phe Leu Cys
TTT GCC AAG CAC AGG AGG TCG CCC GGA GAG CGG TTC CTG TGC
```

FIGURE 1C

```
Gly Gly Ile Leu Ile Ser Ser Cys Trp Ile Leu Ser Ala Ala
GGG GGC ATA CTC ATC AGC TCC TGC TGG ATT CTC TCT GCC GCC

His Cys Phe Gln Glu Arg Phe Pro Pro His His Leu Thr Val
CAC TGC TTC CAG GAG AGG TTT CCG CCC CAC CAC CTG ACG GTG

Ile Leu Gly Arg Thr Tyr Arg Val Val Pro Gly Glu Glu Glu
ATC TTG GGC AGA ACA TAC CGG GTG GTC CCT GGC GAG GAG GAG

Gln Lys Phe Glu Val Glu Lys Tyr Ile Val His Lys Glu Phe
CAG AAA TTT GAA GTC GAA AAA TAC ATT GTC CAT AAG GAA TTC

Asp Asp Asp Thr Tyr Asp Asn Asp Ile Ala Leu Leu Gln Leu
GAT GAT GAC ACT TAC GAC AAT GAC ATT GCG CTG CTG CAG CTG

Lys Ser Asp Ser Ser Arg Cys Ala Gln Glu Ser Ser Val Val
AAA TCG GAT TCG TCC CGC TGT GCC CAG GAG AGC AGC GTG GTC

Arg Thr Val Cys Leu Pro Pro Ala Asp Leu Gln Leu Pro Asp
CGC ACT GTG TGC CTT CCC CCG GCG GAC CTG CAG CTG CCG GAC

Trp Thr Glu Cys Glu Leu Ser Gly Tyr Gly Lys His Glu Ala
TGG ACG GAG TGT GAG CTC TCC GGC TAC GGC AAG CAT GAG GCC

Leu Ser Pro Phe Tyr Ser Glu Arg Leu Lys Glu Ala His Val
TTG TCT CCT TTC TAT TCG GAG CGG CTG AAG GAG GCT CAT GTC

Arg Leu Tyr Pro Ser Ser Arg Cys Thr Ser Gln His Leu Leu
AGA CTG TAC CCA TCC AGC CGC TGC ACA TCA CAA CAT TTA CTT

Asn Arg Thr Val Thr Asp Asn MET Leu Cys Ala Gly Asp Thr
AAC AGA ACA GTC ACC GAC AAC ATG CTG TGT GCT GGA GAC ACT

Arg Ser Gly Gly Pro Gln Ala Asn Leu His Asp Ala Cys Gln
CGG AGC GGC GGG CCC CAG GCA AAC TTG CAC GAC GCC TGC CAG

Gly Asp Ser Gly Gly Pro Leu Val Cys Leu Asn Asp Gly Arg
GGC GAT TCG GGA GGC CCC CTG GTG TGT CTG AAC GAT GGC CGC
```

FIGURE 1D

```
MET Thr Leu Val Gly Ile Ile Ser Trp Gly Leu Gly Cys Gly
ATG ACT TTG GTG GGC ATC ATC AGC TGG GGC CTG GGC TGT GGA

Gln Lys Asp Val Pro Gly Val Tyr Thr Lys Val Thr Asn Tyr
CAG AAG GAT GTC CCG GGT GTG TAC ACC AAG GTT ACC AAC TAC

Leu Asp Trp Ile Arg Asp Asn MET Arg Pro
CTA GAC TGG ATT CGT GAC AAC ATG CGA CCG TGACCAGGAA

CACCCGACTC CTCAAAAGCA AATGAGATCC CGCCTCTTCT TCTTCAGAAG
ACATACTTCC CATTTTGGAA GTTTTCAGGA CTTGGTCTGA TTTCAGGATA
CTCTGTCAGA TGGGAAGACA TGAATGCACA CTAGCCTCTC CAGGAATGCC
TCCTCCCTGG GCAGAAAGTG GCCATGCCAC CCTGTTTTCA GCTAAAGCCC
AACCTCCTGA CCTGTCACCG TGAGCAGCTT TGGAAACAGG ACCACAAAAA
TGAAAGCATG TCTCAATAGT AAAAGATAAC AAGAGATCTT TCAGGAAAGA
CGGATTGCAT TAGAAATAGA CAGTATATTT ATAGTCACAA GAGCCCAGCA
GCGGCTCAAA GTTGGGCAG GCTGGCTGGC GTCATGTTCC TCAAAAGCAC
CTTGACGTCA AGTCTCCTTC CCCTTTCCCC ACTCCCTGGC TCTCAGAAGG
TATTCCTTTT GTGTACAGTG TGTAAAGTGT AATCCTTTTT CTTTATAAAC
TTTAGAGTAG CATGAGAGAA TTGTATCATT TGAACAACTA GGCTTCAGCA
TATTTATAGC AATCCATGTT AGTTTTTACT TTCTGTTGCC ACAACCCTGT
TTTATACTGT ACTTAATAAA TTCAGATATA TTTTTCACAG TTTTTCCAAA
AAAAAAAAA A
```

TRUNCATED THROMBOLYTIC PROTEINS

This application is a continuation in part of U.S. Pat. Ser. Nos. 825,104, filed Jan. 31, 1986 now abandoned; 853,781, filed Apr. 18, 1986 now abandoned; and 861,699, filed May 9, 1986 now abandoned; the contents of which are hereby incorporated herein by reference.

This invention relates to substances having tissue plasminogen activator-type (t-PA) activity. More specifically, this invention relates to "recombinant" thrombolytic proteins, a process for obtaining the proteins from genetically engineered cells, and the therapeutic use of the substances as thrombolytic agents.

These proteins are active thrombolytic agents which, it is contemplated, possess improved fibrinolytic profiles. This may be manifested as increased affinity to fibrin, increased fibrinolytic activity and/or prolonged biological half-life. It is also contemplated that proteins of this invention can be more conveniently prepared in homogeneous form than can native human t-PA. An improved overall pharmacokinetic profile is contemplated for these proteins.

The polypeptide backbone of natural human t-PA includes four consensus Asn-linked glycosylation sites. It has been shown that two of these sites are typically glycosylated in t-PA from melanoma-derived mammalian cells, i.e. at $Asn_{117}$ and $Asn_{448}$. $Asn_{184}$ is glycosylated sometimes and $Asn_{218}$ is typically not glycosylated. t-PA from melanoma-derived mammalian cells, e.g. Bowes cells, is also referred to herein as "native" or "natural" human t-PA.

This invention involves novel proteins which are truncated variants of human t-PA. These variants are characterized by deletion of 1–94 amino acids from $Gly_{-3}$ or $Ser_1$ through $Thr_{91}$, with reference to the peptide sequence of human t-PA, and by t-PA-type thrombolytic activity. Notwithstanding these deletions, the numbering of amino acids as shown in FIG. 1 is retained herein.

These variants may further contain no N-linked carbohydrate moieties or may be only partially glycosylated relative to natural human t-PA. A "partially glycosylated" protein, as the phrase is used herein, means a protein which contains fewer N-linked carbohydrate moieties than does native human t-PA. This absence of glycosylation or only partial glycosylation results from amino acid substitution at one or more of the concensus N-linked glycosylation recognition sites present in the native t-PA molecule. N-linked glycosylation recognition sites are presently believed to comprise tripeptide sequences which are specifically recognized by the appropriate cellular glycosylation enzymes. These tripeptide sequences are either asparagine-X-threonine or asparagine-X-serine, where X is usually any amino acid. A variety of amino acid substitutions at one or more of the three positions of a glycosylation recognition site, especially the first and/or third such positions, results in non-glycosylation at the modified tripeptide sequence. By way of example, $Asn_{117}$ and $Asn_{184}$ of t-PA have both been replaced with Thr in one embodiment and with Gln in another embodiment. At least in the case of the double Gln replacement, the resultant glycoprotein ($Gln_{117}Gln_{184}$) should contain only one N-linked carbohydrate moiety (at $Asn_{448}$) rather than two or three such moieties as in the case of native t-PA. Those skilled in the art will appreciate that analogous glycoproteins having the same $Asn_{448}$ monoglycosylation may be prepared by substituting other amino acids at positions 117 and 184 and/or by substituting one or more amino acids at other positions within the respective glycosylation recognitions sites, e.g. at $Ser_{119}$ and $Ser_{186}$, as mentioned above and/or by substitution at one or more of the "X" positions of the tripeptide sites. In another embodiment Asn at positions 117, 184 and 448 are replaced with Gln. The resultant truncated variant should contain no N-linked carbohydrate moieties, rather than two or three such moieties as in the case of native t-PA. In other embodiments, potential glycosylation sites have been modified individually, for instance by replacing Asn, e.g. with Gln, at position 117 in one presently preferred embodiment, at position 184 in another embodiment and at position 448 in still another embodiment. This invention encompasses such non-glycosylated, monoglycosylated, diglycosylated and triglycosylated truncated t-PA variants.

These variants may be described schematically with reference to the polypeptide of formula (1) below:

$$(a)A\text{-}R^1\text{-}B\text{-}R^2\text{-}C\text{-}R^3\text{-}D \qquad (1)$$

wherein A, B, C and D represent the following domains of t-PA, substantially as depicted in FIG. 1: A is the polypeptide sequence $Gly_{-3}$ or $Ser_1$ through $Trp_{116}$ encompassing domain "a", B is $Ala_{120}$ through $Gly_{183}$, C is $Ala_{187}$ through $Leu_{447}$ and D is $Val_{451}$ through $Pro_{527}$ "a" is a peptide sequence of 0 to 93 amino acids selected from within the sequence $Gly_{-3}$ or $Ser_1$ through $Thr_{91}$ present in human t-PA and depicted in FIG. 1. "a" may be a continuous peptide sequence or may comprise a fusion of two or more shorter sequences selected from within the sequence $Gly_{-3}$ or $Ser_1$ through $Thr_{91}$. In one embodiment ($\Delta$EGF), "a" comprises the sequence $Gly_{-3}$ or $Ser_1$ through Ser-50 followed by $Thr_{88}$ through $Thr_{91}$. That embodiment is thus characterized by a continuous polypeptide sequence comprising $Gly_{-3}$ or $Ser_1$ through $Ser_{50}$ followed by $Thr_{88}$ through $Pro_{527}$ In another embodiment ($\Delta$FBR), "a" comprises the sequence $Gly_{-3}$ or $Ser_1$ through $Cys_6$ followed by the sequence $Ser_{52}$ through $Thr_{91}$ That embodiment is thus characterized by a continuous polypeptide sequence comprising $Gly_{-3}$ or $Ser_1$ through $Cys_6$ followed by $Ser_{52}$ through $Pro_{527}$. In a further embodiment ($\Delta$EGF/FBR), "a" comprises the sequence $Gly_{-3}$ or $Ser_1$ through $Ile_5$ followed by $Asp_{87}$ through $Thr_{91}$ That embodiment is thus characterized by a continuous polypeptide sequence comprising $Gly_{-3}$ or $Ser_1$ through $Ile_5$ followed by $Asp_{87}$ through $Pro_{527}$. $R^1$, $R^2$, and $R^3$ of formula (1) above each represent a tripeptide sequence linking the aforementioned polypeptide domains A, B, C and D by peptide bonds. In the compounds of this invention, up to three of the tripeptides $R^1$, $R^2$ and $R^3$ are tripeptide sequences other than consensus glycosylation sites, as described above.

BRIEF DESCRIPTION OF THE DRAWING

In FIG. 1, wild type codons corresponding to $R^1$, $R^2$, and $R^3$ are underlined; arrows indicate $Gly_{-3}$ and $Ser_1$; wild type region in which domain "a" is derived is underlined twice.

Tripeptide sequences other than consensus glycosylation sites present in the polypeptide sequence of human t-PA are tabulated below in Table 1.

TABLE 1

| | Alternative Tripeptide Sequences | | |
|---|---|---|---|
| (wt) | $R^1$ (Asn Ser Ser) | $R^2$ (Asn Gly Ser) | $R^3$ (Asn Arg Thr) |
| I | U Ser Ser | V Gly Ser | V Arg Thr |
| II | Asn W Ser | Asn X Ser | Asn Y Thr |
| III | Asn Ser Z | Asn Gly Z | Asn Arg U |

U = any amino acid except Asn, Thr or Ser
V = any amino acid except Asn
W = any amino acid except Ser
X = any amino acid except Gly
Y = any amino acid except Arg
Z = any amino acid except Thr or Ser
wt = wild type, i.e., prior to mutagenesis By way of example, several glycoproteins of this invention are depicted below in Table 2.

TABLE 3

Exemplary Compounds
(a)A—$R^1$—B—$R^2$—C—$R^3$—D**

| Compound | a | $R^1$ | $R^2$ | $R^3$ |
|---|---|---|---|---|
| 1 | * | Asn Ser Ser | Asn Gly Ser | Asn Arg Thr |
| 2 | # | Asn Ser Ser | Asn Gly Ser | Asn Arg Thr |
| 3 | + | Asn Ser Ser | Asn Gly Ser | Asn Arg Thr |
| 4 | * | Gln Ser Ser | Asn Gly Ser | Asn Arg Thr |
| 5 | # | Gln Ser Ser | Asn Gly Ser | Asn Arg Thr |
| 6 | + | Gln Ser Ser | Asn Gly Ser | Asn Arg Thr |
| 7 | * | Asn Ser Ser | Gln Gly Ser | Asn Arg Thr |
| 8 | # | Asn Ser Ser | Gln Gly Ser | Asn Arg Thr |
| 9 | + | Asn Ser Ser | Gln Gly Ser | Asn Arg Thr |
| 10 | * | Asn Ser Ser | Asn Gly Ser | Gln Arg Thr |
| 11 | # | Asn Ser Ser | Asn Gly Ser | Gln Arg Thr |
| 12 | + | Asn Ser Ser | Asn Gly Ser | Gln Arg Thr |
| 13 | * | Asn Ser Ser | Gln Gly Ser | Gln Arg Thr |
| 14 | # | Asn Ser Ser | Gln Gly Ser | Gln Arg Thr |
| 15 | + | Asn Ser Ser | Gln Gly Ser | Gln Arg Thr |
| 16 | * | Gln Ser Ser | Asn Gly Ser | Gln Arg Thr |
| 17 | # | Gln Ser Ser | Asn Gly Ser | Gln Arg Thr |
| 18 | + | Gln Ser Ser | Asn Gly Ser | Gln Arg Thr |
| 19 | * | Gln Ser Ser | Gln Gly Ser | Asn Arg Thr |
| 20 | # | Gln Ser Ser | Gln Gly Ser | Asn Arg Thr |
| 21 | + | Gln Ser Ser | Gln Gly Ser | Asn Arg Thr |
| 22 | * | Gln Ser Ser | Gln Gly Ser | Gln Arg Thr |
| 23 | # | Gln Ser Ser | Gln Gly Ser | Gln Arg Thr |
| 24 | + | Gln Ser Ser | Gln Gly Ser | Gln Arg Thr |

**A, B, C and D are as defined above; mutagenized positions are underlined; non-mutagenized R groups bear N-linked carbohydrate moieties covalently bonded thereto
* =G.., or $Ser_1$ through $Ser_{50}$ followed by $Thr_{88}$ through $Thr_{91}$ (ΔEGF);
=C.., or $Ser_1$ through $Cys_6$ followed by $Ser_{52}$ through $Thr_{91}$ (ΔFBR);
+ =$Gly_{-3}$ or $Ser_1$ through $Ile_5$ followed by $Asp_{87}$ through $Thr_{91}$ (ΔEGF/FBR).

Table 3 depicts exemplary Thr-substituted analogs of compoounds shown in Table 2.

TABLE 4

Thr Analogs
(a)A—$R^1$—B—$R^2$—C—$R^3$—D**

| Compound | a | $R^1$ | $R^2$ | $R^3$ |
|---|---|---|---|---|
| 25 | * | Asn Ser Ser | Thr Gly Ser | Asn Arg Thr |
| 26 | # | Asn Ser Ser | Thr Gly Ser | Asn Arg Thr |
| 27 | + | Asn Ser Ser | Thr Gly Ser | Asn Arg Thr |
| 28 | * | Asn Ser Ser | Asn Gly Ser | Thr Arg Thr |
| 29 | # | Asn Ser Ser | Asn Gly Ser | Thr Arg Thr |
| 30 | + | Asn Ser Ser | Asn Gly Ser | Thr Arg Thr |
| 31 | * | Asn Ser Ser | Thr Gly Ser | Thr Arg Thr |
| 32 | # | Asn Ser Ser | Thr Gly Ser | Gln Arg Thr |
| 33 | + | Asn Ser Ser | Thr Gly Ser | Thr Arg Thr |
| 34 | * | Thr Ser Ser | Asn Gly Ser | Thr Arg Thr |
| 35 | # | Thr Ser Ser | Asn Gly Ser | Thr Arg Thr |
| 36 | + | Thr Ser Ser | Asn Gly Ser | Thr Arg Thr |
| 37 | * | Thr Ser Ser | Thr Gly Ser | Asn Arg Thr |
| 38 | # | Thr Ser Ser | Thr Gly Ser | Asn Arg Thr |
| 39 | + | Thr Ser Ser | Thr Gly Ser | Asn Arg Thr |
| 40 | * | Thr Ser Ser | Thr Gly Ser | Thr Arg Thr |
| 41 | # | Thr Ser Ser | Thr Gly Ser | Thr Arg Thr |
| 42 | + | Thr Ser Ser | Thr Gly Ser | Thr Arg Thr |

**As in Table 2

In one subgenus of the invention the proteins contain at least one so-called "complex carbohydrate" sugar moiety characteristic of mammalian glycoproteins. As exemplified in greater detail below, such "complex carbohydrate" glycoproteins may be produced by expression of a DNA molecule encoding the desired polypeptide sequence in mammalian host cells. Suitable mammalian host cells and methods for transformation, culture, amplification, screening, and product production and purification are known in the art. See e.g. Gething and Sambrook, Nature 293:620–625 (1981), or alternatively, Kaufman et al., Molecular and Cellular Biology 5 (7):1750–1759 (1985) or Howley et al., U.S. Pat. No. 4,419,446.

A further aspect of this invention involves truncated t-PA variants as defined above in which each carbohydrate moiety is a processed form of the initial dolicol-linked oligosaccharide characteristic of insect cell-produced glycoproteins, as opposed to a "complex carbohydrate" substituent characteristic of mammalian glycoproteins, including mammalian derived t-PA. Such insect cell-type glycosylation is referred to herein as "high mannose" carbohydrate for the sake of simplicity. For the purpose of this disclosure, complex and high mannose carbohydrates are as defined in Kornfeld et al., Ann. Rev. Biochem. 54: 631–64 (1985). "High mannose" variants in accordance with this invention are characterized by a variant polypeptide backbone as described above and as exemplified in Tables 2 and 3.

Such variants may be produced by expression of a DNA sequence encoding the variant in insect host cells. Suitable insect host cells as well as methods and materials for transformation/transfection, insect cell culture, screening and product production and purification useful in practicing this aspect of the invention are known in the art. Glycoproteins so produced also differ from natural t-PA and from t-PA produced heretofore by recombinant engineering techniques in mammalian cells in that the variants of this aspect of the invention do not contain terminal sialic acid or galactose substituents on the carbohydrate moieties or other protein modifications characteristic of mammalian derived glycoproteins.

The truncated proteins of this invention which contain no N-linked carbohydrate moieties may also be produced by expressing a DNA molecule encoding the desired variant, e.g. compounds 22-24 of Table 2, in mammalian, insect, yeast or bacterial host cells. Other truncated proteins of this invention which lack N-linked carbohydrate moieties may be produced by expressing the DNA encoding, e.g. Compounds 1-21, in bacterial cells. As indicated above suitable mammalian and insect host cells, and in addition, suitable yeast and bacterial host cells, as well as methods and materials for transformation/transfection, cell culture, screening and product production and purification useful in practicing this aspect of the invention are also known in the art.

Additionally, as should be clear to those of ordinary skill in this art, this invention also contemplates other t-PA variants which are characterized, instead of by amino acid deletion within the region $Gly_{-3}$ or $Ser_1$ through $Thr_{91}$, by one or more amino acid substitutions within that region, especially in the region $Arg_7$ through $Ser_{50}$, or by a combination of deletion and substitution. cDNAs encoding these compounds may be readily prepared, e.g., by methods closely analogous to the mutagenesis procedures described herein using appropriate mutagenesis oligonucleotides. The cDNAs may be optionally mutagenized at one or more of the codons for $R^1$, $R^2$ and $R^3$, and may be inserted into expression vectors and expressed in host cells by the methods disclosed herein. It is contemplated that these proteins will share the advantageous pharmacokinetic properties of the other compounds of this invention, and perhaps avoid undue antigenicity upon administration in pharmaceutical preparations analogous to those disclosed herein.

As should be evident from the preceding, all variants of this invention are prepared by recombinant techniques using DNA sequences encoding truncated analogs which may also contain fewer or no potential glycosylation sites relative to natural human t-PA. Such DNA sequences may be produced by conventional site-directed mutagenesis of DNA sequences encoding t-PA.

DNA sequences encoding t-PA have been cloned and characterized. See e.g., D. Pennica et al., Nature (London) 301:214(1983) and R. Kaufman et al., Mol. Cell. Biol.5(7): 1750 (1985). One clone, ATCC 39891, which encodes a thrombolytically active t-PA analog is unique in that it contains a Met residue at position 245 rather than Val. Typically, the DNA sequence encodes a leader sequence which is processed, i.e., recognized and removed by the host cell, followed by the amino acid residues of the full length protein, beginning with Gly.Ala.Arg.Ser.Tyr.Gln. . . Depending on the media and host cell in which the DNA sequence is expressed, the protein so produced may begin with the Gly.Ala..Arg amino terminus or be further processed such that the first three amino acid residues are proteolytically removed. In the latter case, the mature protein has an amino terminus comprising Ser.Tyr.Gln. . . . t-PA variants having either amino terminus are thrombolytically active and are encompassed by this invention. Variants in accord with the present invention also include proteins having either $Met_{245}$ or Val $_{245}$, as well as other variants, e.g. allelic variations or other amino acid substitutions or deletions, which still retain thrombolytic activity.

This invention also encompasses compounds as described by formula (1) which contain a further modification in polypeptide domain C. Specifically, compounds of this embodiment are further characterized by an amino acid other than Asn at position 218 and/or an amino acid other than Pro at position 219 and/or an amino acid other than Ser or Thr at position 22o. Compounds of this embodiment thus lack the consensus N-linked glycosylation site which is typically not glycosylated in t-PA produced by melanoma-derived mammalian cells.

As mentioned above, DNA sequences encoding individual variants of this invention may be produced by conventional site-directed mutagenesis of a DNA sequence encoding human t-PA or analogs or variants thereof. Such methods of mutagenesis include the M13 system of Zoller and Smith, Nucleic Acids Res. 10:6487-6500 (1982); Methods Enzymol. 100: 468-500 (1983); and DNA 3:479-488 (1984), using single stranded DNA and the method of Morinaga et al., Bio/technology, 636-639 (July 1984), using heteroduplexed DNA. Several exemplary oligonucleotides used in accordance with such methods to effect deletions in domain A or to convert an asparagine residue to threonine or glutamine, for example, are shown in Table 4. It should be understood, of course, that DNA encoding each of the glycoproteins of this invention may be analogously produced by one skilled in the art through site-directed mutagenesis using(an) appropriately chosen oligonucleotide(s). Expression of the DNA by conventional means in a mammalian, yeast, bacterial, or insect host cell system yields the desired variant. Mammalian expression systems and the variants obtained thereby are presently preferred.

The mammalian cell expression vectors described herein may be synthesized by techniques well known to those skilled in this art. The components of the vectors such as the bacterial replicons, selection genes, enhancers, promoters, and the like may be obtained from natural sources or synthesized by known procedures. See Kaufman et al., J. Mol Biol., 159:51-521 (1982); Kaufman, Proc Natl. Acad, Sci. 82:689-693 (1985).

Established cell lines, including transformed cell lines, are suitable as hosts. Normal diploid cells, cell strains derived from in vitro culture of primary tissue, as well as primary explants (including relatively undifferentiated cells such as haematopoetic stem cells) are also suitable. Candidate cells need not be genotypically deficient in the selection gene so long as the selection gene is dominantly acting.

The host cells preferably will be established mammalian cell lines. For stable integration of the vector DNA into chromosomal DNA, and for subsequent amplification of the integrated vector DNA, both by conventional methods, CHO (Chinese hamster Ovary) cells are presently preferred. Alternatively, the vector DNA may include all or part of the bovine papilloma virus genome (Lusky et al., Cell, 36:391-401 (1984) and be carried in cell lines such as C127 mouse cells as a stable episomal element. Other usable mammalian cell lines include HeLa, COS-1 monkey cells, mouse L-929 cells, 3T3 lines derived from Swiss, Balb-c or NIH mice, BHK or HaK hamster cells lines and the like.

Stable transformants then are screened for expression of the product by standard immunological or enzymatic assays. The presence of the DNA encoding the variant proteins may be detected by standard procedures such as Southern blotting. Transient expression of the DNA encoding the variants during the several days after introduction of the expression vector DNA into suitable host cells such as COS-1 monkey cells is measured without selection by activity or immunologic assay of the proteins in the culture medium.

In the case of bacterial expression, the DNA encoding the variant may be further modified to contain different codons for bacterial expression as is known in the art and preferably is operatively linked in-frame to a nucleotide sequence encoding a secretory leader polypeptide permitting bacterial expression, secretion and processing of the mature variant protein, also as is known in the art. The compounds expressed in mammalian, insect, yeast or bacterial host cells may then be recovered, purified, and/or characterized with respect to physicochemical, biochemical, and/or clinical parameters, all by known methods.

These compounds have been found to bind to monoclonal antibodies directed to human t-PA, and may thus be recovered and/or purified by immunoaffinity chromatography using such antibodies. Furthermore, these compounds possess t-PA-type enzymatic activity, i.e., compounds of this invention effectively activate plasminogen in the presence of fibrin to evoke fibrinolysis, as measured in an indirect assay using the plasmin chromogenic substrate S-2251 as is known in the art.

This invention also encompasses compositions for thrombolytic therapy which comprise a therapeutically effective amount of a variant described above in admixture with a pharmaceutically acceptable parenteral carrier. Such composition can be used in the same manner as that described for human t-PA and should be useful in humans or lower animals such as dogs, cats and other mammals known to be subject to thrombotic cardiovascular problems. It is contemplated that the compositions will be used both for treating and desireably for preventing thrombotic conditions. The exact doseage and method of administration will be determined by the attending physician depending on the potency and pharmacokinetic profile of the particular compound as well as on various factors which modify the actions of drugs, for example, body weight, sex, diet, time of administration, drug combination, reaction sensitivities and severity of the particular case.

The following examples are given to illustrate embodiments of the invention. It will be understood that these examples are illustrative, and the invention is not to be considered as restricted thereto except as indicated in the appended claims.

In each of the examples involving insect cell expression, the nuclear polyhedrosis virus used was the L-1 variant of the *Autographa Californica*, and the insect cell line used was the *spodoptera frugiperda* IPLB-SF21 cell line (Vaughn, J. L. et al., In Vitro (1977) 13, 213–217). The cell and viral manipulations were as detailed in the literature (Pennock G. D., et al., supra: Miller, D. W., Safer, P., and Miller, L. K., Genetic Engineering, Vol. 8, pages 277-298, J. K. Setlow and A. Hollaender, eds. Plenum Press, 1986). The RF m13 vectors, mp18 and mp 11, are commercially available from New England Biolabs. However, those of ordinary skill in the art to which this invention pertains will appreciate that other viruses, strains, host cells, promoters and vectors containing the relevant cDNA, as discussed above, may also be used in the practice of each embodiment of this invention.

The DNA manipulations employed are, unless specifically set forth herein, in accordance with Maniatis et al., Molecular Cloning: A Laboratory Manual (Cold Spring Harbor, N.Y. 1982).

TABLE 4

| | Exemplary Oligonucleotides for Mutagenesis | |
|---|---|---|
| No. | Sequence | Mutation |
| 1. | ACC AAC TGG <u>ACC</u> AGC AGC GCG | $Asn_{117} \longrightarrow Thr$ |
| 2. | CTAC TTT GGG <u>ACT</u> GGG TCA GC | $Asn_{184} \longrightarrow Thr$ |
| 3. | GTGCACCAACTGG<u>CAG</u>AGCAGCGCGTTGGC | $Asn_{117} \longrightarrow Gln$ |
| 4. | CAACTGG<u>CAG</u>AGCAGCG | (#3)* |
| 5. | ACTGCTACTTTGGG<u>CAG</u>GGGTCAGCCTACC | $Asn_{184} \longrightarrow Gln$ |
| 6. | CTTTGGG<u>CAG</u>GGGTCAG | (#5)* |
| 7. | CATTTACTT<u>CAG</u>AGAACAGTC | $Asn_{448} \longrightarrow Gln$ |
| 8. | GGA GCC AGA TCT TAC CAA GTG ATC TGC AGC GAG CCA AGG TGT TTC AAC GGG GGC | (ΔFBR) |
| 9. | TGATC TGC AGC GAG CC | (#8)* |
| 10. | A AGA GGA GCC AGA TCT TAC CAA GTG ATC GAT ACC AGG GCC ACG TGC TAC GAG | (ΔFBR/EGF) |
| 11. | CAA GTG ATC GAT ACC AG | (#10)* |
| 12. | TCA GTG CCT GTC AAA AGT ACC AGG GCC ACG TGC TAC | (ΔEGF) |

TABLE 4-continued

Exemplary Oligonucleotides for Mutagenesis

| No. | Sequence | Mutation |
|-----|----------|----------|
| 13. | GTC AAA AGT ACC AGG G | (#12)* |

*Used for screening the mutation indicated in parenthesis (where a screening oligonucleotide is not indicated, the same oligonucleotide is used for mutagenesis and screening). Codons for replacement amino acids are underlined.
‾ indicates site of deletion. As those skilled in this art will appreciate, oligonucleotides can be readily constructed for use in inserting a different replacement amino acid at a desired site by substituting the codon for the desired amino acid in the oligonucleotide. Other mutagenesis oligonucleotides can be designed based on an approximately 20-50 nucleotide sequence spanning the desired site, with replacement or deletion of the original codon(s) one wishes to change.

PLASMID DERIVATIONS

Mutagenesis of cDNAs at codons for glycosylation site amino acids was conducted using an appropriate restriction fragment of the cDNA in M13 plasmids by the method of Zoller and Smith. Deletions within the cDNA were effected by loopout mutagenesis using an appropriate restriction fragment, e.g. the SacI fragment, of the cDNA either in M13 vectors or by heteroduplex loop-out in plasmid pSVPA4.

The plasmid pSVPA4 was constructed to allow the expression of t-PA glycoprotein in mammalian cells. This plasmid was made by first removing the DNA encoding the SV40 large T polypeptide from the plasmid pspLT5 (Zhu, Z. et al., 1984, J. Virology 51:170-180). This was accomplished by performing a total Xho 1 digest followed by partial Bam-H1 restriction endonuclease digestion. The SV40 large T encoding region in pspLT5 was replaced with human t-PA-encoding sequence by ligating a cohesive SalI/ BamH1 t-PA encoding restriction fragment, isolated by digesting plasmid J205 (ATCC No. 39568) with Sal I and BamH1, to the parent XhoI/BamH1 cut vector pspLT5 prepared as described above. Consequently, t-PA will be transcribed in this vector under the control of the SV40 late promoter when introduced into mammalian cells. This final construct is designated pSVPA4.

Plasmid pLDSG is an amplifiable vector for the expression of t-PA in mammalian cells such as CHO cells. pLDSG contains a mouse DHFR cDNA transcription unit which utilizes the adenovirus type 2 major late promoter (MLP), the simian virus 40 (SV40) enhancer and origin of replication, the SV40 late promoter (in the same orientation as the adenovirus MLP), a gene encoding tetracyclin resistance and a cDNA encoding human t-PA (Val-245) in the proper orientation with respect to the adenovirus type 2 MLP. The preparation of pLDSG from pCVSVL2 (ATCC No. 39813) and a t-PA encoding cDNA has been described in detail as has cotransformation with, and amplification of, pLDSG in CHO cells.. Kaufman et al., Mol. and Cell. Bio. 5(7): 1750-1759 (1985).

Plasmid pWGSM is identical to pLDSG except that the cDNA insert encodes Met-245 human t-PA. pWSGM may be constructed using cDNA from plasmid J205 (ATCC No. 39568) or pIVPA/1 (ATCC No. 39891). Throughout this disclosure pWGSM and pLDSG may be used interchangeably, although as indicated previously, the former vector will produce Val-245 proteins and the latter Met-245 proteins.

pIVPA/1 (ATCC No. 39891) is a baculoviral transplacement vector containing a t-PA-encoding cDNA. pIVPA/1 and mutagenized derivatives thereof are used to insert a desired cDNA into a baculoviral genome such that the cDNA will be under the transcriptional control of the baculoviral polyhedrin promoter.

HETERODUPLEX MUTAGENESIS

The mutagenesis via heteroduplexed DNA of specific areas in the t-PA expression plasmid, pSVPA4, involves the following steps:
Preparation of ampicillin sensitive pSVPA4 DNA
1. Plasmid pSVPA4 (15 ug) was linearized with PvuI to completion. This mixture was extracted with phenol/chloroform and the DNA was precipitated using two volumes of ethanol with 0.1 M NaCl present.
2. The DNA was resuspended in a 21 ul of water, 1 ul dNTB solution (containing 2mM dATP, dGTP, dTTP, dCTP), 2.5 ul 10X nick translation buffer (0.5M Tris-Cl pH 7.5, 0.1 M MgSO$_4$, mM DTT, 500 ug/ml) and 0.5 ul (2 units) DNA polymerase 1-Large Fragment (New England Biolabs). This mixture was incubated at room temperature for thirty minutes and then phenol/chlorform extracted followed by ethanol precipitation as described above.
3. The precipitated DNA was resuspended to 0.2 ug/ul by the addition of 75 ul water.

Preparation of ampicillin resistant pSVPA4 DNA
1. Plasmid pSVPA4 (15 ug) was digested with Sac I which cuts this plasmid twice within the t-PA encoding sequence to produce two restriction fragments, a 1.4 kbp t-PA encoding restriction fragment plus the parent vector. Following restriction digestion 1 ul (28 units) of calf intestine alkaline phosphatase (Boehringer Mannheim) was added then incubated at 37° C. for five minutes. The two bands were separated by loading this mixture onto a 0.7% agarose gel. The parent vector restriction fragment was excised from the gel and extracted by adsorption to silica dioxide at 4° C., which was followed by elution in 50 mM Tris/1mM EDTA at 37° C. for thirty minutes. The eluted DNA was adjusted to a final concentration of 0.2 ug/ul.

Heteroduplex Annealing
1. Mix 6 ul (1.2 ug) of ampicillin sensitive pSVPA4 DNA with 6 ul (1.2 ug) ampicillin resistant pSVPA4 DNA.
2. Add an equal volume (12 ul) of 0.4 M NaOH. Incubate at room temperature for ten minutes.
3. Slowly add 4.5 volumes (108 ul) of 0.1 M Tris-Cl pH 7.5/20 mM HCl.
4. 50 picomoles (5 ul) of phosphorylated mutagenic oligonucleotide was added to 45 ul of heteroduplex mixture.
5. This mixture was incubated at 68° C. for two hours then slowly cooled to room temperature.

Mutagenesis
1. Each mutagenesis reaction was adjusted to the following concentrations by the addition of 7 ul to the heteroduplex mixtures, 2mM MgCl/0.2 mM ATP/60uM dATP, dTTP,dGTP,dCTP/4 mM DTT/40 units/ml Klenow fragment of E. coli DNA polymerase I (B.R.L.), 2000 units/ml T4 DNA ligase (N.E.B.). This mixture was incubated at room temperature for 2 hours.

2. The reaction was then phenol/chloroform extracted which was followed by ethanol precipitation. The precipitated DNA was resuspended in 12 ul 50mM Tris-Cl/1mM EDTA. 4ul of this was used to transform competent HB101 bacteria.

3. Ampicillin resistant colonies were screened with $1 \times 10^6$ cpm/ml of a $^{32}$P-labeled screening oligonucleotide in 5X SSC, 0.1% SDS, 5Xdenhardt's reagent, and 100 ug/ml denatured salmon sperm DNA.

4. The filters were washed with 5X SSC, 0.1% SDS at a temperature 5° below the calculated melting temperature of the oligonucleotide probe.

5. DNA was prepared from positively hybridizing clones and analyzed initially by digestion with different restriction enzymes and agarose gel electrophoresis. DNA was transferred to nitrocellulose and filters were prepared and hybridized to the screening probes in order to ensure the mutagenic oligonucleotide was introduced in to the correct fragment.

6. DNA was then retransformed into E. coli and ampicillin resistant colonies were screened for hybridization to the screening oligonucleotide.

7. Final mutations were confirmed by DNA sequencing (Sanger).

Preparation of Mutagenized CdnaS: m13 Method

The following schematic restriction map illustrates a cDNA encoding human t-PA (above) with cleavage sites indicated for specific endonucleases (indicated below):

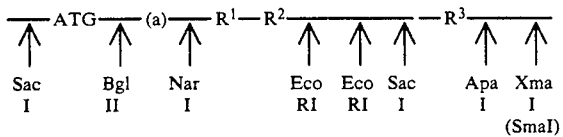

The initiation codon, ATG, and the cDNA regions encoding (a), $R^1$, $R^2$ and $R^3$ are indicated. Thus, mutagenesis resulting in truncation may be effected using the SacI fragment or the BglII/NarI fragment, for example. Mutagenesis at $R^1$ and/or $R^2$ may be effected using, e.g., the SacI fragment, BglII/EcoRI fragment or BglII/SacI fragment. Mutagenesis at $R^3$ may be effected using, an EcoRI/XmaI or EcoRI/ApaI fragment. The choice of restriction fragment may be determined based on the convenience of using particular vectors for mutagenesis and/or for expression vector construction.

Generally, the cDNA restriction fragment to be mutagenized may be excised from the full-length cDNA present, e.g., in pWGSM, pIVPA/1 or pSVPA4, using the indicated endonuclease enzyme(s) and then mutagenized, e.g. with the oligonucleotides shown in Table 4.

Exemplary mutagenized cDNA fragments which may thus be prepared are shown in Table 5, below.

TABLE 5

Exemplary Mutagenized cDNA Fragments

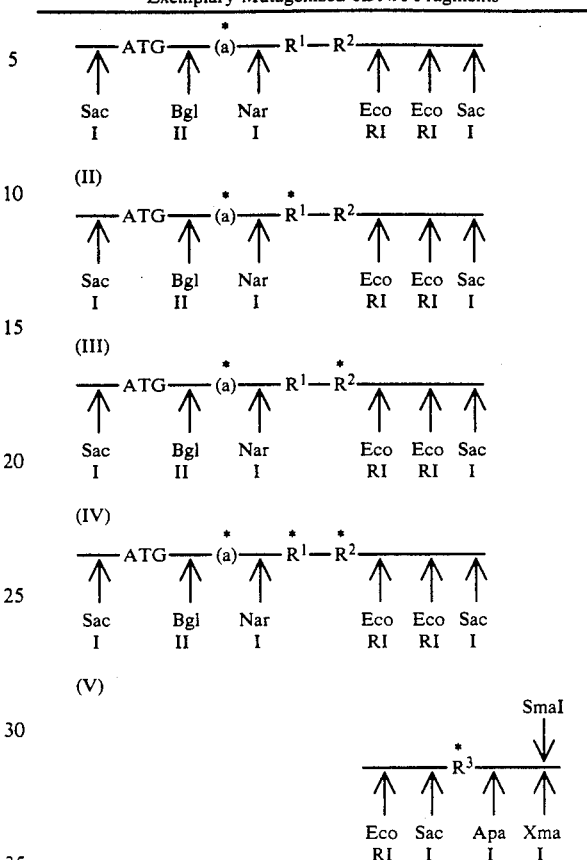

*indicates site of mutagenesis; cDNA fragments I through IV are prepared by digesting pWGSM or pSVPA4 with SacI, inserting SacI fragment into M13 vector, mutagenizing with desired oligonucleotide(s), and digesting mutagenized M13/t-PA DNA with SacI; alternatively, I-IV may be excised from mutagenized M13/t-PA with BglII and SacI and the BglII/SacI fragment encoding the peptide domain spanning a, $R^1$ and $R^2$ may be inserted into BglII/SacI-digested pIVPA; cDNA fragment V is prepared as described in Example 2, below.

Following mutagenesis the fragment, with or without further mutagenesis, may then be excised from the M13 vector and ligated back into an expression vector containing the full-length or partial cDNA previously cleaved with the same enzyme(s) as were used for excising the mutagenized fragment from the M13 vector. By this method the full-length cDNA, mutagenized as desired, may be re-assembled using one or more mutagenized fragments as restriction fragment cassettes.

cDNAs encoding the following compounds (see Table 2) may be prepared from the mutagenized fragments of Table 5 as follows:

| Compound | Route |
|---|---|
| 1-3 | (a) ligate mutagenized cDNA fragment I (prepared using oligonucleotides #8,10 or 12) into SacI-digested pSVPA4, or excise fragment I from mutagenized M13/t-PA as the BglII/SacI fragment and insert same into BglII/SacI-digested pIVPA/1. |
| 4-6 | (b) ligate mutagenized cDNA fragment II (prepared using oligonucleotides #8,10 or 12 and then oligonucleotide #3) into SacI-digested pSVPA4, or excise fragment II from mutagenized M13/t-PA as the BglII/SacI fragment and insert same into BglII/SacI-digested pIVPA/1. |
| 7-9 | (c) ligate mutagenized cDNA fragment III |

-continued

| Compound | Route | |
|---|---|---|
| | | (prepared using oligonucleotides #8,10 or 12 and oligonucleotide #5) into SacI-digested pSVPA4 or excise fragment III from mutagenized M13/t-PA as the BglII/SacI fragment and insert same into BglII/SacI-digested pIVPA/1. |
| 10–12 | (d) | digest mutagenized pIVPA/1 or pSVPA4 produced by Route (a) with EcoRI (partial digest) and XmaI (SmaI) or ApaI (total digest) to remove wild type $R^3$ coding region, and ligate thereto mutagenized cDNA fragment V (prepared using oligonucleotide #7) as the EcoRI/ApaI or EcoRI/XmaI (SmaI) fragment. |
| 13–15 | (e) | digest mutagenized pIVPA or pSVPA prepared as in Route (c) with EcoRI (partial digest) and XmaI (SmaI) or ApaI (total digest) to remove wild type $R^3$-coding region, and ligate thereto cDNA fragment V (prepared using oligonucleotide #7) as the EcoRI/ApaI or EcoRI/XmaI (SmaI) fragment. |
| 16–18 | (f) | digest mutagenized pIVPA or pSVPA4 prepared by Route (b) with EcoRI (partial digest) and XmaI (SmaI) or ApaI (total digest) and ligate thereto mutagenized cDNA fragment V (prepared using oligonucleotide #7) as the EcoRI/ApaI or EcoRI/XmaI (SmaI) fragment. |
| 19–21 | (g) | ligate mutagenized cDNA fragment IV (prepared using oliogonucleotides #8,10 or 12 and oligonucleotides #3 and 5) into SacI-digested pSVPA4 or excise fragment IV from mutagenized M13/t-PA as the BglII/SacI fragment and ligate same into BglII/SacI-digested pIVPA/1. |
| 22–24 | (h) | ligate mutagenized cDNA fragment IV (prepared using oligonucleotides #8,10 or 12 and oligonucleotides #3 and 5) into SacI-digested pSVPA4 prepared by Routes (d), (e) or (f) or ligate fragment IV so produced as the BglII/SacI fragment into BglII/SacI-digested pIVPA produced by Route(s) (d), (e), of (f). |

Plasmids pIVPA or pSVPA4, in addition to utility as expression vectors, may also be used as a "depot" in the construction of cDNAs having any desired permutation of mutagenized sites. Thus, "pIVPA/Δ" or "pSVPA4/Δ", mutagenized (via M13 or heteroduplexing) plasmids containing a desired deletion in domain A (i.e. containing a cDNA region encoding a desired "a" region) may be digested with NarI (partial) and XmaI (SmaI) (total) to remove the cDNA region encoding the protein domain spanning $R^1$, $R^2$ and $R^3$. A second pIVPA or pSVPA4 plasmid mutagenized, if desired (via M13 or heteroduplexing), at any combination of $R^1$, $R^2$ and $R^3$-encoding regions may then be digested with NarI (total) and XmaI (SmaI) (total) and the NarI/XmaI (SmaI) fragment may then be identified, isolated and ligated into the NarI/XmaI (SmaI) digested pIVPA/Δ or pSVPA4/Δ. Such use of the NarI/XmaI (SmaI) restriction fragment cassette, for example, allows the construction of desired mutagenized cDNAs in pIVPA or pSVPA4. The mutagenized cDNA may then be transferred, e.g. as a BglII/XmaI restriction fragment cassette into BglII/XmaI-digested pWGSM for mammalian expression, if desired.

EXAMPLES

Example 1

Preparation of $Gln_{117}$ Deletions Variants

A. Preparation of Gln-117 truncated cDNA cDNA molecules encoding the polypeptide sequence of compounds 4–6 of Table 2 were prepared using the oligonucleotide-directed mutagenesis method of Zoller and Smith. Specifically, the mutagenesis vector RF M13/t-PA containing the t-PA gene was constructed from the mammalian t-PA expression plasmid pSVPA4. RF M13/t-PA was constructed by first digesting pSVPA4 to completion with the restriction endonuclease SacI. The approximately 1,436 base pair (bp) SacI fragment encodes a large portion of the polypeptide sequence of t-PA and includes the nucleotide sequences encoding the consensus N-linked glycosylation sites encompassing asparagines 117, 184, and 218. This 1,436 bp (hereinafter 1.4 kbp) fragment was purified by preparative agarose gel electrophoresis.

The Sac I fragment of the t-PA cDNA, obtained as a SacI fragment, above, was ligated to a linearized double-stranded RF M13mp18 DNA vector which had been previously digested with Sac I. The ligation mixture was used to transform transformation competent bacterial JM101 cells. M13 plaques containing t-PA-derived DNA produced from transformed cells were identified and isolated by analytical DNA restriction analysis and plaque hybridization. Radiolabeled oligonucleotides (~17mers, of positive polarity) derived from within the SacI restriction sites of the t-PA-encoding nucleotide sequence depicted in FIG. 1 were used as probes in the plaque hybridization. All oligonucleotides were prepared by automated synthesis with an Applied Biosystems DNA synthesizer according to the manufacturer's instructions.

Several of the hybridization positive plaques were then further cloned by conventional plaque purification. Purified M13/t-PA bacteriophage obtained from the plaque purification procedure was used to infect JM101 cells. These infected cells produce cytoplasmic double-stranded "RF" M13/t-PA plasmid DNA. The infected cells also produce bacteriophage in the culture medium which contains single-stranded DNA complimentary to the 1.4 kbp SacI fragment of t-PA and to M13 DNA. Single-stranded DNA was purified from the M13/t-PA-containing phage isolated from the culture medium. This single-stranded M13/t-PA DNA was used as a template in a mutagenesis reaction according to the method of Zoller and Smith using oligonucleotide #3 of Table 4. This mutagenesis event changes the Asn codon to a Gln codon at position 117 of the subsequently obtained coding strand of DNA by changing the DNA sequence from "AAC" to "CAG". Following the mutagenesis reaction, the DNA was transformed into the bacterial strain JM 101. To identify mutagenized cDNA's, the transformant plaques were screened by DNA hybridization using radiolabeled oligonucleotide #4 of Table 4, All exemplary oligonucleotides in Table 4 are of positive polarity, i.e., represent portions of a coding rather than non-coding strand of DNA. All hybridization positive plaques were further purified by subsequent secondary infections of JM 101 cells with M13 phage containing mutagenized DNA.

RF M13/t-PA plasmid DNA was purified from JM 101 cells infected with purified M13 phage containing mutagenized t-PA cDNA. The RF M13/t-PA plasmid thus obtained contains the Gln117 mutagenized Sac I restriction fragment of t-PA DNA.

This mutagenized restriction fragment can then be further mutagenized, again by the method of Zoller and Smith, but using the oligonucleotides described below. The oligonucleotides described below were designed to induce a deletion ("loop out") within the cDNA region encoding the A domain. In the truncated proteins encoded by the deletion-mutagenized cDNAs so produced, the amino acid or amino acid sequence, if any, remaining from $Gly_{-3}$ or $Ser_1$ through $Thr_{91}$ is referred to herein as domain "a".

Deletion Mutagenesis 1

Oligonucleotide #8 of Table 4 induced a cDNA deletion encoding $Arg_7$ through $Cys_5$, inclusive. Following this second mutagenesis reaction the DNA is transformed into JM 101 cells. To identify mutagenized cDNAs, the transformant plaques were screened as above, but using radiolabeled oligonucleotide #9 of Table 4. Hybridization positive plaques can be further purified by subsequent secondary infections of JM 101 cells with M13 phage containing the twice mutagenized t-PA cDNA. The cDNA prepared as described below which contains this mutagenized restriction fragment encodes compound #5 of Table 2 in which $Cys_6$ is covalently bonded to $Ser_{51}$ by a peptide bond.

Deletion Mutagenesis 2

Oligonucleotide #10 of Table 4 induced a cDNA deletion encoding $Cys_6$ through $Ile_{86}$, inclusive. Following this second mutagenesis reaction the DNA is transformed into JM 101 cells. To identify mutagenized cDNAs, the transformant plaques were screened as above, but using radiolabeled oligonucleotide #11 of Table 4. Hybridization positive plaques can be further purified by subsequent secondary infections of JM 101 cells with M13 phage containing the twice mutagenized t-PA cDNA. The cDNA prepared as described below which contains this mutagenized fragment encodes compound #6 of Table 2 in which $Ile_5$ is covalently bonded to $Asp_{87}$ by a peptide bond.

Deletion Mutagenesis 3

Oligonucleotide #12 of Table 4 can be used to generate a cDNA deletion encoding $Cys_{51}$ through $Asp_{87}$, inclusive. Following this second mutagenesis reaction the DNA is transformed into JM 101 cells. To identify mutagenized cDNAs, the transformant plaques were screened as above, but using radiolabeled oligonucleotide #13 of Table 4. Hybridization positive plaques can be further purified by subsequent secondary infections of JM 101 cells with M13 phage containing the twice mutagenized t-PA cDNA. The cDNA prepared as described below which contains this mutagenized restriction fragment encodes compound #4 of Table 2 in which $Ser_{50}$ is covalently bonded to $Thr_{88}$ by a peptide bond.

Each of these mutagenized restriction fragments can then be ligated back into the mammalian expression vector pSVPA4 as a Sac I cassette by methods analogous to those described in Example #3B, or prepared for insertion into the insect cell expression vector pIVPA/1 (ATCC No.39891) as a Bgl II/Sac I cassette derived from modified RF M13/t-PA.

B. Preparation of Vectors Used for Expression of High Mannose $Gln_{117}$ Deletion Variants The purified RF M13/t-PA containing the modified and truncated t-PA cDNA, prepared as described above, can be digested with the restriction endonucleases BglII and Sac I. The approximately 1.2 kbp BglII/Sac I restriction fragment was purified by conventional preparative gel electrophoresis. The BglII/Sac I fragment so obtained constitutes a mutagenized cassette which lacks a 5' and 3' portion of the DNA which encodes the amino and carboxy termini of the translated protein.

Insect expression vector pIVPA/1 (ATCC No. 39891) contains a wild type tPA cDNA insert operatively linked to a polyhedrin promoter together with baculovirus flanking DNA sequences. pIVPA/1 was digested with BglII and Sac I thereby excising a t-PA coding region spanning domains A, B and C. The BglII/Sac I cassettes containing the mutagenized, truncated t-PA cDNA fragments may each then be ligated to pIVPA/1 expression vector DNA which had been previously purified following digestion with BglII and SacI. The resulting plasmids, pIVPA/ΔFBR, $Gln_{117}$; pIVPA/ΔFBR/ΔEGF, $Gln_{117}$; pIVPA/ΔEGF, $Gln_{117}$ should contain the mutagenized cDNAs encoding compounds 5, 6 and 4 respectively, now operatively linked to the polyhedrin promoter. The nucleotide sequence of each mutagenized cDNA insert may be confirmed by supercoil sequencing with plasmid as substrate. See e.g, E. Y. Chen et al., 1985, DNA 4(2):165-170.

B. Introduction of the Mutagenized cDNA into the Insect Virus

Each of the pIVPA plasmids containing the mutagenized cDNAs may be introduced into the insect virus by co-transfection with wild-type AcNPV in *Spodoptera* cells. 1 ug of purified *Autographa californica* NPV DNA and 10ug of the desired pIVPA DNA are introduced into *Spodoptera* cells growing on tissue culture dishes by a calcium phosphate transfection procedure (Potter, K. N. and Miller, L. K., J. Invertebr. Path. (1980), 36 431-432). The joint introduction of these DNAs into the cells results in a double recombination event between the pIVPA plasmid (containing the mutagenized cDNAs) and the viral DNA at the regions of homology between the two; that is, the polyhedrin gene region of the progeny virus from the recombination event contains the mutagenized cDNA insert from the pIVPA plasmid.

Isolation of Virus Containing the Nucleotide Sequence Encoding Compound 1

The progeny virus present in the media over the transfected cells are plaqued onto a fresh monolayer of cells at several different dilutions. Plaques are assayed, and the recombinants are picked based on the PIB-minus phenotype as follows: A virus which has lost its polyhedrin gene, as would a virus containing a mutagenized cDNA will not produce PIBs. Plaques that appear PIB deficient are selected, excised and amplified on fresh cells. The supernatant over these cells is then assayed for t-PA-type enzymatic activity. Positive assay results indicate that the glycoprotein is in fact being produced.

An alternative method of virus purification via the plaque lifting protocol differs slightly from the steps described above, and is described below. Plaque the progeny virus from transfection at suitable dilution onto cell culture dishes. Prepare a nitrocellulose replica of the cell monolayer and the virus plaques. Reserve the agarose overlay from the plate as the virus source after the results of the following steps are obtained.

Probe the nitrocellulose filter with radioactive DNA fragments representative of the gene being placed into the viral chromosome. Score positives as those containing the foreign gene. Remove the hybridized probe. Re-probe the filter with radioactive DNA representative of a portion of the viral chromosome removed by substitution with the foreign DNA. One would score positives as those which still have a polyhedrin gene.

Remove the hybridized probe. Re-probe the filter with a radioactive DNA fragment which will identify viral plaques regardless of the state of the polyhedrin gene. A suitable fragment may be the EcoRI I fragment. Score these as progeny virus. Select those plaques which are positive for the foreign gene DNA probe, negative for the polyhedrin gene probe, and positive for the viral DNA probe. These are strong candidates for the desired genotype.

C. Production and Characterization of High Mannose Glycoprotein

Antibodies have been used to demonstrate the presence of the variant proteins in the extracellular media of infected cells. Recombinant virus, prepared as above, is used to infect cells grown in the usual TC-100 (Gibco) nutrient salts solution but instead of the standard media supplement of 10% fetal calf serum, this is replaced with a 50% egg yolk enrichment (to 1% total volume) (Scott Biologicals). Previous experiments had demonstrated a more intact protein under these conditions. The supernatant from the infected cells is fractionated on an affinity column bearing an attached monoclonal antibody to natural human t-PA. Protein specifically retained by the column is eluted and assayed for t-PA enzymatic activity. A fixed amount of activity units of this and control t-PA preparations are separated on an acrylamide gel. This gel is then stained with a silver-based reagent to display the protein pattern. This reveals that the virus, upon infection of insect cells, leads to the extracellular production of a protein having t-PA type activity.

Radiolabeled protein is produced for further characterization by first incubating *spodoptera frugiperda* cells infected with the virus (m.o.i=1) for 48 hours. The culture plates are then rinsed with methionine-deficient media. Methionine-deficient media supplemented with $^{35}S$-methione is then added to the culture plates. The cell cultures are incubated for 4 hours. The supernatant containing the radiolabeled glycoprotein may be analyzed by SDS-PAGE (7.5%) against wild type (i.e. full-length fully glycosylated) t-PA analogously produced in insect cells and against mammalian t-PA produced e.g. by the method of R. Kaufman et al., Mol. Cell. Biol. 5(7):1750(1985)., but in the presence of tunicamycin (non-glycosylated). The partially glycosylated truncated proteins produced in Example 1 should have an increased gel mobility relative to the fully-glycosylated analog and to the non-glycosylated full-length analog.

EXAMPLE 2

PREPARATION OF OTHER TRUNCATED PROTEINS.

A. Preparation of other cDNA's

The mutagenesis methods of Example 1 can be used with other synthetic oligonucleotides which modify the original t-PA DNA sequence to produce truncated proteins optionally modified at N-linked glycosylation sites with the appropriate codon change(s) illustrated in Table 1. See, e.g. "Preparation of Mutagenized cDNAs: M13 Method" and Routes (a)-(h), supra.

For example, cDNA encoding Compounds #1,2 and 3 may be prepared using the SacI restriction fragment in M13/t-PA and mutagenizing with oligonucleotides #8, 10 and 12 respectively, but not with oligonucleotide #3. Vector construction, transfection and expression may be carried out as in Example 1 for insect cells or as described below in Example 3 for mammalian cells.

Single-stranded DNA generated from the M13 mutagenesis vector (RF M13/t-PA), prepared as in Example 1, can also be used as a template to mutagenize, in a site specific manner, at glycosylation site(s) $R^1$ or $R^2$ or both. The region encoding the consensus tripeptide which encompasses $Asn_{218}$ may be similarly mutagenized. To prepare multiple modifications of the protein at these sites an iterative process may be used. For example, following the identification and the purification of M13 phage containing a modified $R^1$ site, single-stranded DNA containing this modified site can be purified from phage and used as template to initiate a second round of mutagenesis within the $R^2$ site. This process can be repeated until all desired modifications are obtained. Thus, cDNA encoding Compounds 7,8 and 9 may be prepared by the method of Example 1 but substituting mutagenesis oligonucleotide #5 for oligonucleotide #3 and screening oligonucleotide #6 for oligonucleotide #4. cDNA encoding Compounds 19,20, and 21 may be prepared by twice mutagenizing the SacI fragment as described in Example 1 and addition mutagenizing and screening with oligonucleotides #5 and #6. Vector construction, transfection and expression are carried out as in Example 1 for insect cells or as described below for mammalian cells. See Routes (a)-(h), supra.

The RF M13/t-PA mutagenesis vector does not contain DNA sequence encoding $R^3$, the N-linked glycosylation site of t-PA most proximal to the carboxy-terminus of the protein. Therefore in order to make DNA modifications at that site, a new M13/t-PA mutagenesis RF vector called M13/t-PA:RI-Xma I was made. This vector was constructed by digesting the M13 vector M13mpII to completion with EcoRI and Xma I. The RI/XmaI digested M13 vector was ligated to a purified EcoRI/Xma I t-PA restriction fragment (approximately 439bp, hereinafter 0.4 kbp) encoding a polypeptide region encompassing glycosylation site $R^3$. This 0.4 kbp restriction fragment was purified following digestion of the plasmid pWGSM with EcoRI and Xma I. The mammalian expression plasmid pWGSM, encoding the t-PA gene, is identical within the 439bp EcoRI/Xma I fragment to the plasmid pLDSG described by Kaufman et al., Mol. Cell Biol. 5:1750-1759 (1985).

The ligation mixture was used to transform competent bacterial JM 101 cells. Several plaques were picked and analyzed for the presence of the 0.4 kbp t-PA EcoRI/XmaI fragment by standard DNA restriction fragment analysis. Double-stranded RF M13 DNA was purified from cells containing the 0.4 kbp t-PA fragment. This DNA was designated RF M13/tPA:RI-Xma I mutagenesis vector. As previously indicated in Example 1A this vector, when transformed into competent JM101 cells, can be used to make M13/t-PA:RI-XmaI phage from which single-stranded M13/t-PA:RI-XmaI DNA can be purified. This single-stranded DNA can be used as template in the site-directed mutagenesis reaction to modify the t-PA DNA at the N-linked glycosylation site $R^3$.

Modified $R^3$ coding sequences can be used to replace the wild-type $R^3$ sequences present in either modified pIVPA/1 as prepared in Example 1 (truncated and/or modified at $R^1$ and/or $R^2$) or wild-type pIVPA/1 plasmid DNA. This can be accomplished by first performing a total Sac I/Apa I digestion of the $R^3$ modified M13/t-PA:RI/XmaI mutagenesis plasmid vector, and isolating the $R^3$ modified 165 base pair t-PA restriction fragment so produced. The insect expression vector pIVPA/1 or pIVPA/1 plasmid DNA modified, e.g. as in Example 1, can similarly be totally digested with Sac I and Apa I to excise the 165 bp wild-type t-PA restriction fragment encoding the unmodified $R^3$ site. Ligation of the purified insect expression vector lacking the 165 bp fragment to the modified $R^3$ 165 bp fragment produces a new insect expression vector. Expression of the vector produces a truncated protein having altered codons at the $R^3$ site, as well as at any or all of the other consensus N-linked glycosylation sites present in natural t-PA.

The pIVPA plasmid containing the modified cDNA may also be used to generate the BglII/ApaI fragment of the modified t-PA cDNA which spans the deletion region in domain A as well as the region encoding $R^1$, $R^2$ and $R^3$ or the NarI/XmaI fragment which spans $R^1$, $R^2$ and $R^3$. Either of those fragments may be inserted into mammalian expression vectors such as pSVPA4 or pWGSM as described in Example 3.

EXAMPLE 3

PREPARATION OF COMPOUNDS 1, 2 AND 3 IN MAMMALIAN CELLS

A. Preparation of cDNA.

cDNA molecules encoding the polypeptide sequences of compounds 1, 2 and 3 of Table 2 were prepared using mutagenesis oligonucleotides #8, 10, and 12, respectively, and the SacI fragment of the t-PA cDNA as template by the M13 method of Example 1 or heteroduplex mutagenesis (Moranaga Heteroduplex Mutagenesis protocol; both, supra). Mutants selected by DNA hybridization using screening oligonucleotides 9, 11 and 13 respectively were confirmed by DNA sequence analysis to be correct in the modified DNA sequence.

B. Modified t-PA Vector Preparation

Each modified cDNA prepared in Example 1A ($\Delta$, Gln$_{117}$) or 3A ($\Delta$) was first removed from the M13 mutagenesis vector RF M13/t-PA by total digestion of the vector with SacI. The approximately 1.4kbp restriction fragment of each mutagenized cDNA was purified by gel electrophoresis and then ligated into pSVPA4 as follows. First, pSVPA4 was digested with SacI to remove the wild type t-PA 1.4kbp restriction fragment. The remaining portion of the SacI digested pSVPA4 was then ligated to the 1.4kbp restriction fragment of the mutagenized cDNA. This ligation event can produce two orientations of the inserted fragment. The appropriate orientation in each case may be identified using EcoRI and PvuII as the enzymes in conventional analytical restriction enzyme analysis. This replacement allows the Sac I fragment to be used as a cassette fragment between the RF M13/t-PA mutagenesis vector and the pSVPA4 mammalian expression vector. Modified M13 SacI fragments (truncated and optionally modified at $R^1$ and/or $R^2$) may be inserted into SacI-digested pSVPA4 DNA which has been previously, or is subsequently, modified at $R^3$ if desired. Alternatively, DNA previously modified at $R^1$, $R^2$ and/or $R^3$ can be excised from vectors such as pIVPA or pSVPA4 as a NarI/ApaI or NarI/XmaI fragment. The fragment so obtained may then be inserted into vectors such as pSVPA4 or pWGSM previously digested with NarI (partial) and ApaI or XmaI (total). By this method any combination of truncation and glycosylation site mutagenesis may be achieved.

C. Transfection of COS (SV40 transformed African Green Monkey Kidney) Cells COS-1 cells (ATCC CRL 1650) were transfected by the method of Lopata, M. A. et al., Nucl. Acids Res. 12:5707-5717 (1984) with the vectors prepared in Example 3B, i.e., modified pSVPA4. Serum containing medium was replaced with serum-free medium 24 hours after the transfection and conditioned medium was assayed for both the presence of plasminogen activating activity, using the chromogenic substrate S-2251, or the presence of t-PA antigen by an ELISA assay, 48 and 72 hours post-transfection.

D. Viral Propagation in CV1 (African Green Monkey Kidney) Cells

Modified complex carbohydrate protein can be produced by infecting CV1 cells (ATCC CCL 70) with SV40 viral stocks propagated as described by Gething and Sambrook (Nature 293:620-625, 1981). This has been carried out by first totally digesting modified pSVPA4 with the restriction endonuclease BamHI to remove the bacterial shuttle vector pXf3 from the SV40 viral DNA. Before transfecting this DNA into CV1 cells, along with the helper virus SV40-rINS-pBR322 DNA (described below), the Bam HI linearized SV40/t-PA DNA is circularized by ligation at dilute DNA concentrations (1 ug/ml). This process was repeated with the insulin containing SV40 vector SV40-rINS-pBR322 (Horowitz, M. et al., 1982, Eukaryotic Viral Vectors, pp. 47-53, Cold Spring Harbor Laboratory). The bacterial shuttle vector pBR322 in SV40-rINS-pBR322 was removed by a total EcoRI digestion. The linearized insulin/SV40 viral DNA was then circularized by ligation at a DNA concentration of 1 ug/ml. It is necessary to transfect CV-1 cells with circular ligated pSVPA4 and SV40-rINS-pBR322 DNAs, at equimolar amounts in order to generate viral stocks. SV40-rINS-pBR322 is used to provide "late" SV40 proteins while pSVPA4 provides the "early" SV40 proteins necessary for virus production. Consequently when cells are transfected with both these DNA's as described by Gething and Sambrook, SV40 virus is produced which contains either viral DNA vectors. Subsequent infection of CV1 cells with amplified virus has produced protein with t-PA-type activity which can be assayed 72 hours post-infection as described in Example 3C.

EXAMPLE 4

Preparation of Other Proteins cDNA encoding the various proteins of this invention have been prepared by the methods of Examples 1, 2 and 3. The Bgl II/XmaI restriction fragment cassette may then be excised from either the pIVPA or pSVPA4 vector containing the cDNA encoding the truncated protein with or without modification at one or more glycosylation sites. The excised BglII/XmaI fragment may then be ligated into Bgl II/XmaI-cut pSVPA4 or pWGSM for introduction into mammalian cells. Expression of such cDNAs in mammalian host cells, e.g. by the method of Example 3 or by the method of Kaufman et al., supra, (CHO host cells) or by the method of Howley et al., U.S. Pat. No. 4,419,446 (1983) (BPV expression systems) yields the corresponding mammalian-derived truncated proteins. Thus, cDNAs encoding compounds #5 (ΔFBR, Gln$_{117}$) and #6 (ΔFBR/EGF, Gln$_{117}$) were prepared and inserted into pSVPA4 as described above. cDNA encoding compound #4 (ΔEGF, Gln$_{117}$) was prepared using mutagenesis oligonucleotide #12 and screening oligonucleotide #13 (Table 4) but by the heteroduplex method described above, with pSVPA4 previously mutagenized at position 117 (as above) as template. Similarly, cDNAs encoding Compounds #2 (ΔFBR) and #3 (ΔEGF/FBR) were prepared by M13 mutagenesis, as described above, and inserted as the SacI fragment into SacI-digested pSVPA4. cDNA encoding Compound #1 (EGF) was prepared by the heteroduplex method, described above, using pSVPA4 as template and mutagenesis oligonucleotide #12, and screening with oligonucleotide #13.

To prepare the cDNAs encoding the truncated proteins for amplification and expression in mammalian cells, cDNA contained in pSVPA4 or pIVPA is excised as a BglII/XmaI fragment and ligated into purified, BglII/XmaI-digested pWGSM.

In each case the resulting pWGSM vector is introduced into CHO cells and amplified by the method of Kaufman, supra. The transformed and amplified CHO cells produce compounds 1, 2, 3, 4, 5 and 6, respectively, which were detected in the culture medium by human t-PA specific antibodies. The compounds may then be recovered and purified by immunoaffinity chromatography.

EXAMPLE 5

Example 4 may be repeated using cDNA encoding the truncated proteins with or without modification at $R^1$, $R^2$, and/or $R^3$ to produce the desired protein in CHO cells. Mutagenized cDNAs may be prepared as described above. Thus, cDNAs encoding Compounds 22, 23 and 24 are prepared in pIVPA as described in Example 2. The cDNAs may then be excised as the BglII/XmaI fragment and ligated into purified, BglII/XmaI-digested pWGSM, and the resultant vector transformed and amplified in CHO cells as in Example 4 to produce compounds 22, 23 and 24.

What is claimed is:

1. A thrombolytic protein having a sequence selected from the group consisting of:
   (i) the peptide sequence of FIG. 1 from Gly$_{-3}$ to Pro$_{527}$;
   (ii) the peptide sequence of FIG. 1 from Ser$_1$ to Pro$_{527}$ and
   (iii) the peptide sequence of either (i) or (ii) modified to contain Val instead of Met at position 245;
   wherein Cys$_6$ through Ile$_{86}$ are deleted and the N-linked glycosylation site at position 117-119 is modified such that Asn$_{117}$ is replaced with Gln, said thrombolytic protein being glycosylated at at least one unmodified N-linked glycosylation site.

2. A thrombolytic protein having tissue plasminogen activating activity produced by expression of a DNA molecule encoding a protein of claim 1 in a host cell selected from the group consisting of insect and mammalian cells.

3. A therapeutic composition for the treatment of thrombotic conditions which comprises an effective amount of a protein of claim 1 in admixture with a pharmaceutically acceptable carrier.

* * * * *